(12) United States Patent
Sakurai et al.

(10) Patent No.: US 6,964,872 B2
(45) Date of Patent: Nov. 15, 2005

(54) IMMUNOASSAY METHOD

(75) Inventors: Masaaki Sakurai, Tokyo (JP); Naoki Takanashi, Tokyo (JP); Masanori Oka, Tokyo (JP); Minoru Hirata, Tokyo (JP)

(73) Assignee: SRL, Inc., Tokyo (JP)

( * ) Notice: Subject to any disclaimer, the term of this patent is extended or adjusted under 35 U.S.C. 154(b) by 20 days.

(21) Appl. No.: 10/450,109

(22) PCT Filed: Apr. 26, 2002

(86) PCT No.: PCT/JP02/04274

§ 371 (c)(1),
(2), (4) Date: Jul. 15, 2003

(87) PCT Pub. No.: WO02/095407

PCT Pub. Date: Nov. 28, 2002

(65) Prior Publication Data

US 2004/0058387 A1    Mar. 25, 2004

(30) Foreign Application Priority Data

May 18, 2001 (JP) .............................. 2001-149938

(51) Int. Cl.[7] .......................................... G01N 33/543
(52) U.S. Cl. ...................... 436/518; 436/525; 436/526; 436/545; 435/7.1; 435/7.91; 435/7.92; 435/7.93; 435/7.94; 435/7.95; 435/7.7
(58) Field of Search ................................ 436/518, 525, 436/526, 545; 435/7.1, 7.91–7.95, 7.7

(56) References Cited

U.S. PATENT DOCUMENTS 5,470,759 A    11/1995   Sugiyama et al. ............ 436/541

FOREIGN PATENT DOCUMENTS

| JP | 4-145367    | 5/1992 |
| JP | 6-66795     | 3/1994 |
| JP | 6-167495    | 6/1994 |
| JP | 7-35752     | 2/1995 |
| JP | 10-10127    | 1/1998 |
| JP | 2000-503763 | 3/2000 |
| WO | 97/22366    | 6/1997 |

*Primary Examiner*—Long V. Le
*Assistant Examiner*—Pensee T. Do
(74) *Attorney, Agent, or Firm*—Wenderoth, Lind & Ponack, L.L.P.

(57) ABSTRACT

When insoluble magnetic carrier particles are used in immunoassay, a method is provided which is suitable for saving labor and for treating a large number of samples within a short time while avoiding problems including difficulties in the stability of sensitized insoluble magnetic particles and in their preparation. In assaying an antigenic substance in test samples, no use is made of insoluble magnetic particles carrying an antibody specific to the said antigenic substance but insoluble magnetic carrier particles are provided in a state free from adsorbing said antibody, etc. Then the antigenic substance per se to be assayed is adsorbed on the insoluble magnetic carrier particles followed by reaction with a labeled antibody specific to the said adsorbed antigenic substance. Thus, the antigenic substance in the test sample can be efficiently assayed in a mode suitable for automation.

10 Claims, 5 Drawing Sheets

| A1c | PBS | BSA | Previous |
|---|---|---|---|
| 0.0 | 46810 | 5506 | 12178 |
| 4.3 | 244065 | 103717 | 63037 |
| 8.0 | 343033 | 175070 | 157811 |
| 11.3 | 414175 | 243168 | 226922 |
| 14.7 | 501599 | 348525 | 254224 |

| Calibrator | Fujikura | VERITAS | | |
| --- | --- | --- | --- | --- |
| | | Epoxy | Carboxylic acid | Amine |
| 0 | 10121 | 1731 | 5016 | 6907 |
| 4.5 | 244578 | 12379 | 192307 | 32155 |
| 7.9 | 473523 | 20169 | 253398 | 46913 |
| 11.1 | 525088 | 26717 | 277308 | 44169 |
| 14.7 | 654123 | 33089 | 325298 | 49881 |

IMMUNOASSAY METHOD

This application is a U.S. national stage of International Application No. PCT/JP02/04274 filed Apr. 26, 2002.

FIELD OF THE INVENTION

The present invention relates to a method for immunologically measuring (immunoassaying for) an antigenic substance in a fluid (such as a biological sample) utilizing a magnetic particle.

BACKGROUND OF THE INVENTION

At hospitals, test centers, etc. in recent years, there have been attempts for automating various tests including clinical tests and/or saving an amount of measuring time in view of a shortage of manpower, cost-cutting purposes, demands for treating large quantities of samples, etc. For the technique suitable for this automation, a method where antigenic substances are subjected to a qualitative or quantitative assay with insoluble magnetic carrier particles has drawn attention. One of the objects for utilizing such insoluble magnetic carrier particles is to readily carry out an unavoidable B/F separation in the assay with a magnetic field action.

In addition, in the immunochemical field where such insoluble magnetic carrier particles are utilized, there have been used antigen or antibody-bound insoluble magnetic particles (sensitized insoluble magnetic particles) wherein the said magnetic carrier carries an antigen or antibody identical with a target analyte to be assayed. The publicly known ones in the present field are those which (for example, as described in JP, A, 06-160387 (1994) and JP, A, 07-72, 155 (1995)) comprise, in the case of assaying for an antigenic substance in a fluid (test sample) such as a biological sample, the step of mixing the said test sample with insoluble magnetic particles on which an antibody capable of specifically binding to the said antigenic substance or a fragment thereof is pre-adsorbed and carried, and the step of then measuring the degree of the said antigenic substance bound to the said insoluble magnetic particles whereupon the said antigenic substance will be detected or quantitated.

However, when antibodies, etc. are previously adsorbed on insoluble magnetic particles and used for the assay, the stability problem of the sensitized insoluble magnetic particles is unavoidable. Therefore, regardless of every effort, there still remain problems including the best-before-period issue of the reagents, difficulty in preparing the same, etc. Further, there is another problem that, when preserved for a long period, the sensitized insoluble magnetic particles are apt to cause precipitates in a suspension thereof.

In the introduction of test instruments for fully-automated clinical tests, etc. for saving labor or for treating large quantities of samples within a short time, it is usually necessary to conduct washing treatments for the B/F separation in the assay. To reduce even a few steps or carry out the assay in a simple fashion is an unavoidable proposition for making the measurement efficient and rapid. For these purposes, it has been recently attempted to develop an immunoassay system where insoluble magnetic particles are used as carriers but it is unavoidable to lose the insoluble magnetic particles used therefor during the washing step. That is also a cause for consuming precious antibodies carried on said carrier, etc. As such, in the automated clinical test instruments using magnetic particles, there is a disadvantage that more antibodies, etc. are required than in the case of usual immunoassay because of the use of relatively large quantities of magnetic particles. In addition, there is a problem in the particle loss due to washing for many times.

SUMMARY OF THE INVENTION

As a result of an intensive investigation, the present inventors have succeeded in finding that upon assays for antigenic substances in test samples, without using any insoluble magnetic carrier particle carrying an antibody specific to the said antigenic substance but with providing an insoluble magnetic carrier particle in such a state where none of said antibodies and the like are substantially adsorbed thereon, said antigenic substance (target analyte to be assayed) itself can be allowed to be adsorbed on the said antibody-free insoluble magnetic carrier particle followed by reaction with a labeled antibody specific to the resultant antigenic substance adsorbed on the said particle whereby the antigenic substance in the test sample can be efficiently assayed in a mode suitable for automation. Thus, the present inventors have succeeded in completing the present invention.

More particularly, the immunoassay of the present invention comprises the steps of providing an insoluble magnetic carrier particle in such a state substantially free of any antibody, etc., then adsorbing or binding an antigenic substance in a test sample to the insoluble magnetic carrier particle, and reacting the resultant mixture with a labeled antibody specifically reactive with the said adsorbed antigenic substance whereby said immunoassay enables the selective measurement of the antigenic substance carried on the insoluble magnetic carrier particle.

In view of making the maintenance of quantitation easy in the present invention, it is preferable that conditions including biomaterial concentrations and concentrations of buffers for insoluble carrier particle suspensions are selected depending on specific assay items so that the antigenic substance in the biomaterial may be adsorbed on the insoluble carrier particle in proportion to its existing amount.

The present invention provides:

(1) An immunoassay using an insoluble carrier particle which comprises (i) using an insoluble magnetic carrier particle in a state substantially free of any adsorbed antigen and/or antibody, (ii) adsorbing an antigenic substance in a test sample on said insoluble magnetic carrier particle or binding the antigenic substance to the said insoluble magnetic carrier particle, (iii) reacting the resultant insoluble magnetic carrier particle from the above treatment (ii) with an antibody being of a labeled antibody specifically reactive with some of the said antigenic substance, said antibody being specifically reactive with a solid-phase form of the antigenic substance, but substantially non-reactive with a native-state form of the antigenic substance, wherein said solid-phase antigenic substance is attached to the said insoluble carrier particle, and said native-state antigenic substance is still present in a liquid phase, and (iv) measuring as an indicator the label on the resultant labeled antibody captured by the said solid-phase antigenic substance;

(2) The immunoassay according to the aforementioned (1), wherein said immunoassay comprises (A) adsorbing said antigenic substance in said test sample on said insoluble magnetic carrier particle or binding the said antigenic substance to the insoluble magnetic carrier particle, and (B) then reacting the captured antigenic substance with said specifically solid-phase antigenic substance-reactive antibody without removing the said test sample with washing;

(3) The immunoassay according to the aforementioned (1) or (2), wherein said immunoassay comprises (a) reacting said labeled antibody with the insoluble magnetic carrier particle that said antigenic substance in said test sample is adsorbed on or bound to, (b) then separating an unreacted labeled antibody from the insoluble magnetic carrier particle in the presence of a magnetic field action, and (c) measuring as an indicator the label on the resultant labeled antibody captured by the said solid-phase antigenic substance;

(4) The immunoassay according to any of the aforementioned (1) to (3), wherein said antibody is monoclonal;

(5) The immunoassay according to any of the aforementioned (1) to (3), wherein said antibody is polyclonal;

(6) The immunoassay according to any of the aforementioned (1) to (5), wherein said insoluble magnetic carrier particle is selected from fine particles wherein said fine particle is substantially insoluble in an aqueous liquid medium and comprised of an organic polymer material phase and a magnetic material phase;

(7) The immunoassay according to any of the aforementioned (1) to (6), wherein said insoluble magnetic carrier particle is selected from fine particles wherein said fine particle comprises not only a coat phase made up of one or more organic polymer materials but also a core phase made up of one or more magnetic materials;

(8) The immunoassay according to any of the aforementioned (1) to (7), wherein said insoluble magnetic carrier particle is selected from latex particles wherein said latex particle has (a) an average particle size ranging from 0.01 to 20 microns and (b) a core made up of one or more magnetic materials;

(9) The immunoassay according to any of the aforementioned (1) to (7), wherein said insoluble magnetic carrier particle is selected from latex particles wherein said latex particle has an average particle size ranging from 0.1 to 6 microns and a core comprised of one or more magnetic materials;

(10) The immunoassay according to any of the aforementioned (1) to (9), wherein said immunoassay is practicable in an automated fashion at steps from dispensing said test sample to attaining test results with an automated clinical test instrument or clinical chemistry autoanalyzer suited for magnetic particles; and

(11) The immunoassay according to any of the aforementioned (1) to (10), wherein the antigenic substance in the test sample is HbA1c.

The above objectives and other objectives, features, advantages, and aspects of the present invention are readily apparent to those skilled in the art from the following disclosures. It should be understood, however, that the description of the specification including the following best mode of carrying out the invention, examples, etc. is illustrating preferred embodiments of the present invention and given only for explanation thereof. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein are mentioned for illustrative purposes, the disclosure of which is hereby incorporated by reference.

BEST MODE FOR CARRYING OUT THE INVENTION

Figure 1:
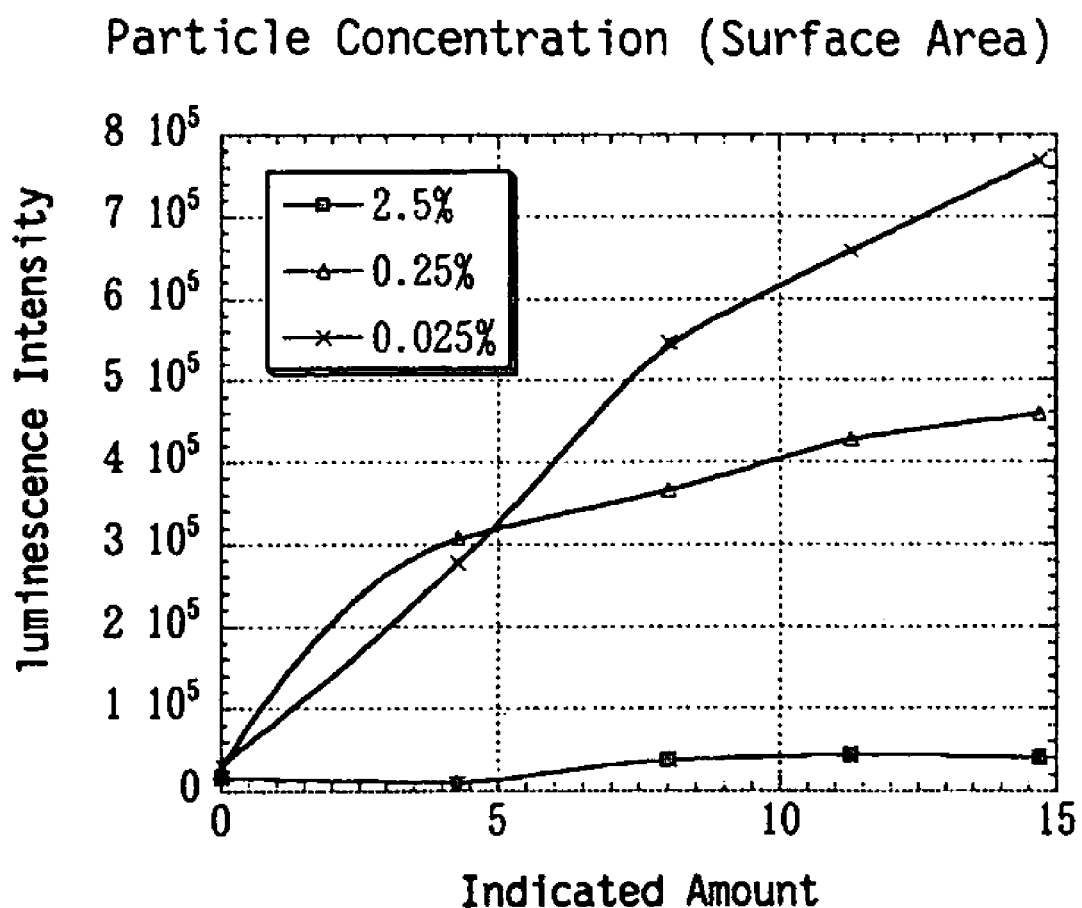
FIG. 1 shows the particle surface area-signal relationship between insoluble magnetic carrier particles and the resultant signals in the HbA1c assay with labeled anti-HbA1c mAb, including the step of adsorbing HbA1c on the magnetic latex particles.

In the present invention, it is possible to react a labeled antibody (labeled Ab), particularly, a labeled monoclonal antibody (labeled mAb), selectively with a specific antigenic substance being adsorbed on or attached to an insoluble magnetic carrier, substantially without reacting said labeled Ab (particularly, said labeled mAb) with said specific antigenic substance being still present in a liquid phase. Accordingly, in a preferable aspect of the present invention, it is possible to adsorb an antigenic substance being present in a test sample on an insoluble carrier, followed by reaction with anti-said antigenic substance mAb in the aforementioned immunoassay without removing the said test sample with washing.

Thus, in a preferred embodiment of the present invention, mAb used herein is selected from those reactive with an antigen being adsorbed on an insoluble carrier particle but substantially non-reactive with an unadsorbed (unbound) antigenic substance present in a liquid phase whereby it is now possible to substantially exclude the interfering action by the un-adsorbed (unbound) component.

(Antigenic Substance)

Antigenic substances to be assayed according to the present invention include any so far as they are capable of being adsorbed on (or attached to) an insoluble magnetic carrier, provided that it is possible to produce or obtain at least one polyclonal or monoclonal antibody against the said specific antigenic substance, but no limitation to the scope of the antigenic substance is intended hereby. In view of facilitating adsorption on the insoluble magnetic carrier, however, it is preferable to select a substance being contained at not less than 100 μg/mL (further not less than 1 mg/mL) or at not less than 1% (of the total protein weight) in a biological sample. In addition, in view of facilitating production of the above-mentioned polyclonal and/or monoclonal antibodies, it is preferable that the aforementioned antigenic substance should be a substance (such as protein) having a molecular weight of not less than 10,000.

The "antigenic substance" to be assayed according to the immunoassay of the present invention includes any as long as at least one polyclonal or monoclonal antibody to the said target antigenic substance is producible or available. The "antigenic substance" includes a variety of substances such as proteins, polypeptides and recombinant proteins produced by means of genetic engineering techniques. They may be either publicly known ones or novel ones in the said immunoassay field. A representative of the antigenic substance is HbA1c.

(Antibody Specific to Antigenic Substance)

As used herein, the term "antibody specifically reactive with an antigenic substance" may cover any of polyclonal antibodies and/or monoclonal antibodies, and also those which are intact molecules or fragments and derivatives thereof, including F(ab')$_2$, Fab' and Fab fragments. Preferable techniques for producing monoclonal antibodies include, for example, the methods using hybridoma cells (G. Kohler and C. Milstein, Nature, 256, pp. 495–497 (1975)); Brodeur et al., Monoclonal Antibody Production Techniques and Applications, pp. 51–63, Marcel Dekker, Inc., New York (1987)), etc. and, besides that, the following documents may be exemplified concerning antibody: J. J. Langone et al. (ed.), "Methods in Enzymology", Vol. 121 (Immunochemical Techniques, Part I: Hybridoma Technology and Monoclonal Antibodies), Academic Press, New York (1986), or documents quoted therein, the disclosure of which is incorporated herein by reference.

Suitably, monoclonal antibodies can be produced by adoptions of cell fusion techniques as reported by Koehler & Milstein (Nature, 256, 495–497, 1975), etc. The said method per se is a conventional technique. Therefore, it will be unnecessary to be particularly illustrated; however, it is required to select target monoclonal antibody-producing hybridoma cells efficiently in this method. Because of its easiness in treating a large number of samples, it is often to conduct the selection by the so-called ELISA (enzyme-linked immunosorbent assay) where a predetermined antigen is solid-phased on a 96-well plate, then made to react with the supernatant of hybridoma cell cultures and further made to react with enzyme-labeled anti-mouse immunoglobulin. Since the antigen is solid-phased in that case, this selection method is acceptable when an assay system can be constituted where the antibody will be made to react under such a solid-phase antigen state, but there are some cases where an antibody non-reactive in an assay system exists among monoclonal antibodies produced by hybridoma cells obtained via the selection by ELISA, said assay system being one where the antigen-antibody interaction is conducted in a liquid phase as in the case of radioimmunoassay (RIA).

Although such a phenomenon per se has been publicly known or commonly known in the present field, when such a monoclonal antibody is used, the immunoassay of the present invention allows a specific reaction with a target antigenic substance being solid-phased on insoluble carrier particles without any inhibition due to the antigenic substance still present in the liquid phase.

Representative monoclonal antibodies include, for example, those disclosed in Japanese Patent No. 2,677,753. Particularly, representative monoclonal antibodies are, for example, monoclonal anti-HbA1c antibodies (anti-HbA1c mAbs) disclosed in Japanese Patent No. 2,677,753.

Although the antibody used is usually IgG, it may also include antibody fragments including F(ab')$_2$, Fab', Fab, etc., which are lower molecules derived from parent antibodies by treatment with a digestive enzyme such as trypsin, papain, pepsin and others, and occasional reduction with a reducing agent such as dithiothreitol and mercaptoethanol. It is further possible to use IgM instead of IgG, or to use fragments which are lower molecules derived from parent IgM by the same treatment as for IgG. It is furthermore possible to use a combination of two or more monoclonal antibodies having different recognition epitopes one another.

(Labeling of Antibody)

The antibody as used herein may be labeled with an appropriate marker.

The label may include enzymes, enzyme substrates, enzyme inhibitors, prosthetic groups, coenzymes, enzyme precursors, apoenzymes, fluorescent substances, pigments, chemoluminescent compounds, luminescent substances, coloring substances, magnetic substances, metal particles such as gold colloids, radioactive substances, etc. The enzyme may include dehydrogenases, oxidoreductases such as reductases and oxidases; transferases that catalyze the transfer of functional groups, such as amino, carboxyl, methyl, acyl, and phosphate groups; hydrolases that hydrolyze bonds such as ester, glycoside, ether, and peptide bonds; lyases; isomerases; ligases; etc. Plural enzymes may be used in a conjugated form for detection.

Enzymatic cycling may also be utilizable for example. Typical enzymes for the label include peroxidases such as horseradish peroxidase; galactosidases such as E. coli beta-D-galactosidase; maleate dehydrogenases; glucose-6-phosphate dehydrogenases; glucose oxidases; gluocoamylases; acetylcholine esterases; catalases; alkaline phosphatases such as calf intestinal alkaline phosphatase and E. coli alkaline phosphatase, etc. When alkaline phosphatase is used, measurements can be done by monitoring or inspecting fluorescence, luminescence, etc., generated with substrates such as umbelliferone derivatives including 4-methyl-umbellipheryl phosphate, phosphorylated phenol derivatives such as nitrophenyl phosphate, luciferin derivatives and dioxetane derivatives; enzymatic cycling systems utilizing NADP; and others. It is also possible to utilize luciferin/luciferase systems. When the reaction takes place with hydrogen peroxide to produce oxygen which can be detected with an electrode or others. The electrode may be a glass electrode, an ionic electrode using an insoluble salt membrane, a liquid-membrane type electrode, a polymer membrane electrode and the like. The enzyme label may be replaced with a biotin label and an enzyme-labeled avidin (streptoavidin). For the label, a plurality of various kinds of labels or markers can be used. In this case, it is possible to perform plural measurements continuously or discontinuously and/or simultaneously or separately.

According to the present invention, signal formation may be done using enzyme-reagent combinations, such as combinations of horseradish peroxidase or other peroxidases with a member selected from 4-hydroxyphenylacetic acid, 1,2-phenylenediamine, tetramethylbenzidine, etc.; combinations of beta-D-galactosidases or glucose-6-phosphate dehydrogenases with a member selected from umbelliferyl galactosides, nitrophenyl galactosides, etc.; and others. The signal may be formed with those capable of enzymatically forming quinole compounds such as hydroquinone, hydroxybenzoquinone, and hydroxyanthraquinone; thiol compounds such as lipoic acid and glutathione; phenol derivatives; ferrocene derivatives; etc.

The fluorescent substances and chemiluminescent compounds may include fluorescein isothiocyanate; Rhodamine derivatives such as Rhodamine B isothiocyanate and tetramethyl Rhodamine isothiocyanate; dancyl chloride (5-(dimethylamino)-1-naphtalenesulfonyl chloride), dancyl fluoride, fluorescamine (4-phenylspiro[furan-2(3H), 1'-(3'H)-isobenzofuran]-3,3'-dione); phycobiliproteins such as phycocyanine and physoerythrin; acridinium salts; luminol compounds such as lumiferin, luciferase and aequorin; imidazoles; oxalic acid esters; chelate compounds of rare earth elements such as europium (Eu), terbium (Tb) and samarium (Sm); coumarin derivatives such as 7-amino-4-methylcoumarin; etc.

Coupling between the antibody and the label can be carried out by techniques including physical method such as adsorption; a chemical method using a coupling agent, etc. or an activated reactant; a method using a chemically interactional coupling. The labelling can be accomplished by the reaction of a thiol group with a maleimide group, the reaction of a pyridyldisulfide group with a thiol group, the reaction of an amino group with an aldehyde group, etc. Additionally, it can be suitably selected from widely known methods, techniques which can be easily put into practice by an artisan skilled in the art, and any of modifications derived therefrom. The coupling agents include, for example, formaldehyde, glutaraldehyde, hexamethylene diisocyanate, hexamethylene diisothiocyanate, N,N'-polymethylene bisiodoacetamide, N,N'-ethylene bismaleimide, ethylene glycol bissuccinimidyl succinate, bisdiazobenzidine, 1-ethyl-3-(3-dimethylaminopropyl) carbodiimide, succinimidyl 3-(2-pyridyldithio)propionate (SPDP), N-succinimidyl 4-(N-maleimidometyl)cyclohexane-1-carboxylate (SMCC), N-sulfosuccinimidyl 4-(N-maleimidomethyl)-cyclohexane-1-carboxylate, N-succinimidyl (4-iodoacetyl)-aminobenzoate, N-succinimidyl 4-(1-maleimidophenyl)butyrate, N-(epsilon-maleimidocaproyloxy)succinimide (EMCS), iminothiolane, S-acetylmercaptosuccinic anhydride, methyl-3-(4'-dithiopyridyl)propionimidate, methyl-4-mercaptobutyrylimidate, methyl-3-mercaptopropionimidate, N-succinimidyl-S-acetylmercaptoacetate, etc.

(Insoluble Magnetic Carrier Particle)

The insoluble magnetic carrier particles as used herein are preferably fine particles wherein the fine particle is substantially insoluble in an aqueous liquid medium and comprises an organic polymer material phase and a magnetic material or substance phase. Representative insoluble magnetic carrier particles are fine particles, each of which comprises not only a coat phase made up of one or more organic polymer materials but also a core phase made up of one or more magnetic materials or substances. The said insoluble magnetic carrier particle may include, for example, fine particles comprising one or more members selected from the group consisting of triiron tetraoxide ($Fe_3O_4$), diiron trioxide (gamma-$Fe_2O_3$), various ferrites, metals such as iron, manganese, nickel, cobalt and chromium, alloys such as cobalt alloys, nickel alloys, manganese alloys, etc.; latex particles, gelatin particles, liposome particles, etc. containing the magnetic particle inside therein; and others. Suitably, the insoluble magnetic carrier particle include latex particles constituted from a latex coat surrounding the core of the said magnetic material or substance. Originally, the term latex means a milky sap oozing out from rubber tree upon cutting or being wounded, but the latex as used herein also refers to a suspension or emulsion in which discontinuous fine particles are suspended or dispersed in an aqueous solution. The insoluble magnetic particles preferably used herein include, but are not limited to, fine particles where the surface of the said magnetic particle core is subjected to a surface treatment with an organic substance, etc.

When immunoassay is carried out quantitatively, such latex particles are usually demanded for their particle size homogeneity or uniformity, the control of their surface state, the choice of their internal structure, etc. at a high level. Such high-quality latex particles suited to test reagent applications can be selected from commercially available products. Organic polymer materials which can be employed for constituting the above particles may include, but are not limited to, those for organic polymer material fine particles as disclosed in the prior art (e.g., JP, A, 58-11575 (1983)). The said organic polymer material includes, for example, hydrophobic polymers such as polystyrene, polyacrylonitrile, poly(methyl methacrylate), polycapramide and polyethylene terephthalate; cross-linked hydrophilic polymers such as polyacrylamide, polymethacrylamide, polyvinylpyrrolidone, poly(vinyl alcohol), poly(2-oxyethyl acrylate), poly(2-oxyethyl methacrylate), poly(2,3-dioxypropyl acrylate), poly(2,3-dioxypropyl methacrylate) and polyethylene glycol methacrylate; copolymers comprising about 2 to 4 kinds of each monomer; and others. Although there is no particular limitation for the material of the latex, preferably used ones are styrene type latexes such as polystyrene latexes, acrylic acid type latexes, etc. The use of latex having a strong surface hydrophobicity (such as polystyrene latex) is preferred in view of facilitating smooth adsorption of proteins or peptides. It is also possible to use various kinds of denatured latexes (such as carboxylic acid-denatured latexes) depending upon necessity. The above-mentioned insoluble carrier as used herein includes preferably latexes such as polystyrene latexes. The particularly preferable latex particles are polystyrene particles prepared by emulsion polymerization methods using no emulsifier. The latex as such will be able to be present stably even without any emulsifier because of repulsion among negative charges one another on the surface. Representative commercially available insoluble magnetic carrier particles are Dynabeads M-270 Epoxy, Dynabeads M-270 Amine, Dynabeads M-270 Carboxylic Acid, Dynabeads M-270 Tosylactivated, Dynabeads M-450 Epoxy and Dynabeads M-450 Tosylactivated (VERITAS Corporation, Japan), IMMUTEX-MAG (JSR Corporation, Japan), and SMG-11 (Fujikura Kasei Co., Ltd., Japan). The carrier particles are also available from Bangs Laboratories, Inc., etc.

The particle size of the insoluble magnetic carrier particles used herein is ranging from 0.01 $\mu$m to 20 $\mu$m. It is preferable to select insoluble magnetic particles having a particle size ranging from 0.1 $\mu$m to 6 $\mu$m. Methods for adsorbing the antigenic substance on the insoluble magnetic particle or binding the antigenic substance to the insoluble magnetic particle may include physical adsorption or binding of the antigenic substance being present in the test sample or chemical bonding of the antigenic substance being present in the test sample. Suitably, it is physically adsorbed or bound.

In order to adsorb, on the latex particles, the antigenic substance contained in the test sample, techniques substantially equivalent to those for attaching an antigen to a plate in ELISA, etc. may be applied with regard to a buffer for suspending the latex particles. Natural aggregation is apt to take place in some latex particles. In that case, it is preferable in view of stability to suspend in a weakly alkaline glycine buffer or borate buffer. With regard to the concentration of the latex, it is preferable to use as a suspension of 0.05 to 1% by weight.

(Antigen-Antibody Interaction)

In the present invention, antigenic substances contained in the test sample are solid-phased (or immobilized) and then made to react with labeled Ab specifically reactive with the said solid-phase antigenic substance to label the captured antigenic substance on an insoluble magnetic carrier comprised of latex, etc. It is preferable that an aqueous solution used therefor contains a surface-active agent (such as Tween 20) at about 0.1 to 0.3% for preventing the adsorption of the said antibody on the insoluble carrier comprised of latex, etc.

There is no particular limitation for a container where the reaction is carried out according to the present invention. It is possible to use a container in an ordinary tube-shaped form (test tube; for example, polystyrene test tube). When easiness in simultaneously treating thousands of samples or hundreds of samples is taken into consideration, it is greatly convenient to use an ELISA plate having a plurality of wells, such as a 96-well ELISA plate (NUNC-IMMUNO PLATE, etc.). As will be mentioned later, in view of making measurements by optical means easier, it is preferable to conduct the reaction using a substantially transparent container. When an autoanalyzer which will be mentioned later is used, it is noted that the reaction is usually carried out in a reactor in the said analyzer.

(Measurement)

There is no particular limitation to the methods of measuring the label level of the insoluble magnetic carrier particles. For example, in case the label is qualitatively or semi-quantitatively measured, it is possible to visually judge the label level of the aforementioned insoluble carrier particles based on comparisons with the turbidity level of known samples. When the said label is quantitatively measured, it is preferable to carry out optical measurements in view of simplicity and convenience.

For methods for optically measuring the label on the insoluble magnetic carrier particles comprised of latex, etc., conventionally known methods can be utilized.

In the present invention, it is possible to carry out measuring treatments for test samples; steps of from sample-dispensing treatments until assay result acquisitions by means of an automated instrument such as a clinical test autoanalyzer for magnetic particles. Such automated instruments (systems) for clinical tests include ADVIA™ (trade name, Bayer), ARCHITECT™ (trade name, Dinabbot), IMx™ (trade name, Dinabbot), Access™ (trade name, Beckmann), ECLusys™ (trade name, Roche Diagnostics), LUMIPULSE™ (trade name, FUJIREBIO), etc. Such instruments have been widely utilized in immunoassay systems (utilizing antigen-antibody interactions) and can be adopted for the present invention without any limitation as long as they are such ones. The characteristic features of these instruments have merits and advantages including capability of measuring multi items in a random access fashion, high assay sensitivity, assayability over a broad range, enablement of assay completion within a short time, high assay precision because all steps from dispensing to obtaining assay results are performed in an automated manner, quite little contamination due to the use of exclusive cartridges, etc.

When antigens are measured in ordinary samples, antibody-sensitized magnetic particles are used in the conventional automated clinical test instruments wherein the steps comprise
(a) first reaction:
(1) reacting the magnetic particle with the antigen in the sample and (2) then washing,
(b) second reaction:
(3) reacting the resultant product with a second antibody (using a label such as an enzyme or fluorescent substance as a marker) to the said antigen and (4) then washing, and
(c) third reaction:
(5) reacting the resultant product with a substrate for the marker, and (6) then measuring.

In accordance with the present invention, however, the number of washing times can be reduced as follows:
(a) first reaction:
(1) reacting magnetic particles with an antigen in a sample,
(b) second reaction:
(2) reacting the resultant product with a second antibody (using a label such as an enzyme or fluorescent substance as a marker) to the said antigen and (3) then washing, and
(c) third reaction:
(5) reacting the resultant product with a substrate for the marker, and (6) then measuring.

As a result, a loss in the particles can be greatly inhibited in the present invention.

In methods for optically detecting the aggregation of latex particles, it is necessary to use relatively large quantities of the particles. In the present invention, however, the amount of substances bound to the particles is detectable. Therefore, both the particles and marker-labeled antibodies allow measurement at a one-tenth or even less amount in the present invention than in the conventional methods.

In accordance with the present invention, it is possible to avoid manufacture problems in connection with antibody complexes used in the conventional methods wherein the problems include difficulty in the process for preparing the same, instability at the concentration in actual use, etc. Thus, use of just single Ab in the present invention provides improved stability of substances but no variation among the manufacturing lots, thereby enabling stable, reliable manufacture. The use of only mAb permits utilization of its merits. For instance, it is possible to eliminate variations among antibody lots and to provide highly reliable reagents with steady quality.

Since the insoluble carrier particle reagent of the present invention is never sensitized with an antigen, etc., reagent kits are greatly improved in connection with problems about lot variations among the particles. Further, the particle comprises not only a core made up of magnetic materials or substances but also an surface made up of plastics and is excellent in antigenic substance-adsorbing or binding property.

Assay instruments where the insoluble magnetic carrier particles applicable in the present invention can be used include, for example, FUJIREBIO LUMIPULS™ (ALP-AMPPD™); Beckmann Coulter Access™ (ALP-Lumigen™PPD); Beckmann Coulter LUMIWARD™ (ALP-Lumigen™PPD); Nippon DPC Corporation "Immulize" (ALP-AMPPD™); Bayer ACS™ (acridinium ester); Ortho Clinical Diagnostics VITROS™ ECi (HRP-Luminol); Precision System Science Co., Ltd. HiMICO™; Dinabbot ARCHITECT™ (acridinium ester); Roche Picolumi™ (ruthenium complex); Tosoh AIA-600II (ALP-4MUP); etc. These instruments may also include those utilizing chemiluminescence with enzymes, electrochemiluminescence with ruthenium complexes, chemiluminescence with acridinium esters, etc.

(Assay Embodiments of Hemoglobin A1c)

As an embodiment which well illustrates the characteristics of the immunoassay according to the present invention, an assay example for hemoglobin A1c (HbA1c) is described below although the inventive immunoassay is not limited to the hemoglobin A1c assay.

The aforementioned "hemoglobin A1c" refers to one specific type of glycosylated (or glycated) hemoglobin that is formed via the nonenzymatical attachment of glucose to the α-amino group of valine, N-terminal amino acid residue of hemoglobin (Hb) β-chain. The amount of blood hemoglobin A1c reflects blood glucose control states in diabetes for a relatively long period. Accordingly, the assay for the HbA1c is clinically quite significant in view of assessing glycemic control (refer to, for example, Nippon-Rinsho, 48, Special Issue, 315–322 (1990)).

Hemoglobin is a heterotetramer, basically consisting of two α-chains and two β-chains. Hemoglobin A1c is characterized in that an N-terminal α-amino group is glycosylated on one of two β-chains. Thus, a characteristic reaction site on hemoglobin A1c is one. In other words, hemoglobin A1c functions as a monovalent antigen in view of reactivity with mAb specific to hemoglobin A1c.

In the immunoassay of the present invention, for measuring hemoglobin A1c, for example, a test sample (such as a hemolyzed blood sample prepared via the addition of purified water to whole blood) can be adsorbed on insoluble magnetic carrier particles (latex-coated magnetic particles) followed by reaction with labeled anti-hemoglobin A1c mAb to selectively label hemoglobin A1c present on the latex coat. Measurement of the selectively labeled marker level allows quantitative assay for the hemoglobin A1c. For example, a standard sample where hemoglobin A1c percentage is known as being measured by HPLC or others is quantitated simultaneously by means of the immunoassay of the present invention to prepare a calibration curve. On the basis of the said calibration curve, it is possible to determine the fraction % value of hemoglobin A1c in unknown samples.

(Anti-HbA1c Monoclonal Antibody)

The anti-HbA1c mAb that can be used herein includes any without any particular limitation so far as it is anti-HbA1c mAb substantially reactive with HbA1c being adsorbed or solid-phased but substantially non-reactive with HbA0 being solid-phased (preferably, said anti-HbA1c mAb further does not react substantially with either HbA1c or HbA0 still present in a liquid phase). When mAb is prepared using a glycated peptide as an immunogen, such a monoclonal antibody can be obtained. Reactivity with HbA1c and HbA0 can be measured, for example, in such a manner as disclosed in Japan Patent No. 2,677,753.

In the present invention, it is preferable that the anti-HbA1c mAb has an HbA1c reactivity of not less than 1.0 (more preferably, not less than 2.0) in terms of an immunoplate reader scale as described in Japan Patent No. 2,677,753. It is also preferable that the anti-HbA1c mAb has an HbA0 reactivity of not more than 0.1 (more preferably, not more than 0.05) in terms of such a scale.

In the present invention, it is preferable that the anti-HbA1c mAb is non-reactive with undenatured HbA1c, with HbA0, nor with denatured HbA0, etc. in a liquid phase even at 10 $\mu$g/mL (or, further 20 $\mu$g/mL) anti-HbA1c mAb while it is reactive with denatured HbA1c in a liquid phase at 1 $\mu$g/mL (or, further 0.5 $\mu$g/mL) anti-HbA1c mAb or less.

A preferred embodiment of the assay for HbA1c according to the present invention will be disclosed herein.

In the present invention, about 1 to 20 $\mu$L (or 2 to 5 $\mu$L) of hemolyzed blood solution is usually dispensed as a test sample into each tube. For hemolyzed blood solutions actually used herein, products obtained via the dilution of a test sample (such as a sample wherein 1 mL of purified water is added to 50 $\mu$L of whole blood) with a glycine buffer, etc. at an about 5 to 10-fold dilution rate can be also used.

Thereafter, an aliquot (about 100 to 300 $\mu$L (or 150 to 200 $\mu$L)) of magnetic latex particle suspension (such as 0.12 $\mu$m magnetic particle-coated latex suspension, 0.2% concentration) is added to each tube which is then allowed to stand at 37° C. for about 1 to 30 min (or 3 to 20 min) so that HbA1c in the sample will be adsorbed on the latex. It is preferable that the magnetic latex particle suspension thus used is a product from the dilution of a magnetic latex particle original solution with a glycine buffer, etc.

Next, to HbA1c adsorbed on the latex is added an aliquot (about 100 to 300 $\mu$L (or 150 to 200 $\mu$L)) of anti-HbA1c mAb (such as mouse ascites-derived mAb) labeled with an appropriate marker, and the mixture is allowed to stand (incubated) at 37° C. for about 2 to 30 min (or 3 to 10 min) so that HbA1c is made to react with said labeled mAb. It is preferable that the concentration of the thus used mAb solution will be set optimal, for example, based on a prepared dilution series of anti-HbA1c mAb. The buffer used for the dilution, may include 0.05 to 0.1M glycine buffer (GBS: glycine buffered saline; pH 8.1 to 8.5, containing 0.15M NaCl), etc. It is preferable that the buffer used for this purpose contains an surface-active agent (such as Tween 20) at about 0.1 to 0.5% (or 0.2 to 0.3%) in view of preventing the physical adsorption of mAb on the latex surface.

In the present field, when latex particles are used as the insoluble magnetic carrier particles, it is uneasy to manufacture latex reagents (latexes on which antigen, antibody, etc. are carried) having an equal quality without exception and to preserve products in a stable state while preventing the occurrence of nonspecific aggregation and precipitation.

In contrast, in accordance with the present invention, the non-sensitization of the insoluble magnetic carrier (latex, etc.) with an antigen and an antibody allows applications of commercially available non-sensitized magnetic latex per se as the said insoluble magnetic carrier. In addition, it is not always necessary that the antibody is a pure product. Further, because of the simple reagent, it is possible to keep its storage stability higher whereby it is advantageous for manufacturers as well. As mentioned herein above, in accordance with the present invention, the reagents can be manufactured in a simple and easy fashion whereby it is now possible to provide methods using reagents having a high stability upon preservation.

In applying the immunoassay of the present invention, assay systems for the targets of the present invention or target substances having a substantially equivalent activity thereto may be constructed by adaptations of technical consideration ordinarily given by artisans in the art over general conditions and operations suitable for each of the methods.

For details of those conventional technical methods, it may be possible to refer to a variety of reviews, texts, books, etc. They are, for example, Hiroshi Irie (ed.), "Radioimmunoassay", Kodansha Ltd., Japan, 1974; Hiroshi Irie (ed.), "Zoku-Radioimmunoassay" (Radioimmunoassay; Second Edition), Kodansha Ltd., Japan, 1979; Eiji Ishikawa et al. (ed.), "Koso Meneki Sokuteiho" (Enzyme Immunoassays), Igaku-Shoin Ltd., Japan, 1978; Eiji Ishikawa et al. (ed.), "Koso Meneki Sokuteiho" (Enzyme Immunoassays) (2nd Edition), Igaku-Shoin Ltd., Japan, 1982; Eiji Ishikawa et al. (ed.), "Koso Meneki Sokuteiho" (Enzyme Immunoassays) (3rd Edition), Igaku-Shoin Ltd., Japan, 1987; H. V. Vunakis et al. (ed.), "Methods in Enzymology", Vol. 70 (Immunochemical Techniques, Part A), Academic Press, New York (1980); J. J. Langone et al. (ed.), "Methods in Enzymology", Vol. 73 (Immunochemical Techniques, Part B), Academic Press, New York (1981); J. J. Langone et al. (ed.), "Methods in Enzymology", Vol. 74 (Immunochemical Techniques, Part C), Academic Press, New York (1981); J. J. Langone et al. (ed.), "Methods in Enzymology", Vol. 84 (Immunochemical Techniques, Part D: Selected Immunoassays), Academic Press, New York (1982); J. J. Langone et al. (ed.), "Methods in Enzymology", Vol. 92 (Immunochemical Techniques, Part E: Monoclonal Antibodies and General Immunoassay Methods), Academic Press, New York (1983); J. J. Langone et al. (ed.), "Methods in Enzymology", Vol. 121 (Immunochemical Techniques, Part I: Hybridoma Technology and Monoclonal Antibodies), Academic Press, New York (1986); J. J. Langone et al. (ed.), "Methods in Enzymology", Vol. 178 (Antibodies, Antigens, and Molecular Mimicry), Academic Press, New York (1989); M. Wilchek et al. (ed.), "Methods in Enzymology", Vol. 184 (Avidin-Biotin Technology), Academic Press, New York (1990); J. J. Langone et al. (ed.), "Methods in Enzymology", Vol. 203 (Molecular Design and Modeling: Concepts and Applications, Part B: Antibodies and Antigens, Nucleic Acids, Polysaccharides, and Drugs), Academic Press, New York (1991); etc. and references quoted in the above documents, the disclosures of which are incorporated herein by reference.

EXAMPLES

The present invention is specifically described by means of the following Examples which are provided only for illustrative purposes, and reference to specific embodiments of the present invention. Although these illustrative examples are provided for disclosing particular embodiments of the present invention, they should not be construed as limiting or restricting the scope of the present invention disclosed herein. It should be understood that various modes will be practicable based on the spirit of the present invention.

All the examples were or can be practiced using standard techniques well or conventionally known to those of ordinary skill in the art unless otherwise specified.

Example 1

Relation Between the Surface Area of Particles and the Resulting Signal

Hemolyzed blood: Blood red cells (5 $\mu$L) collected from human were hemolyzed by addition of purified water (500 $\mu$L) and the resultant mixture was used as a test sample.

Biotin-labeled anti-HbA1c mAb: NHS-LC-Biotin (No. 21335; Pierce) was used as a biotinylating reagent. Anti-HbA1c mAb was biotinylated according to the manual attached to the said biotinylating reagent. Unreacted biotin was removed by repeating a dialysis. The anti-HbA1c mAb used is one as disclosed in U.S. Pat. No. 2,677,753 (for this monoclonal antibody, the anti-HbA$_{1c}$ agent enclosed in the hemoglobin A1c (HbA1c) test reagent, "RAPIDIA AUTO HbA1c" (seller: FUJIREBIO Inc., Japan; manufacturer: SRL, Inc., Japan) may be used as well).

For the insoluble magnetic carrier particles, SMG-11 (Fujikura Kasei Co., Ltd., Japan) was used. This magnetic latex particle product had the following physical properties: particle size (nm): 990 and density: 1.58. The insoluble magnetic carrier particles were diluted with water to form an aqueous dilution series: 2.5%, 0.25% and 0.025%. In 100 $\mu$L of 2.5% aqueous magnetic latex particle dilution, the number of particles was 3.12E+0.9 and the surface area (m$^2$) was 9.59E-03; in the case of 0.25% dilution, the number of particles was 3.12E+0.8 and the surface area (m$^2$) was 9.59E-04; and in the case of 0.025% dilution, the number of particles was 3.12E+0.7 and the surface area (m$^2$) was 9.59E-05.

To 100 $\mu$L of aqueous magnetic latex particle dilution was added 5 $\mu$L of hemolyzed blood solution and the mixture was allowed to stand at room temperature for 5 min to adsorb antigenic substances thereon. Thereafter, 50 $\mu$L of 0.07 mg/ml biotinylated anti-HbA1c mAb was added thereto. The mixture was allowed to stand at room temperature for 5 min and washed once with an ALP buffer (1% BSA, 50 mM imidazole, 150 mM NaCl, 1 mM MgCl$_2$, 0.1 mM ZnCl$_2$, 0.05% Tween 20; pH 7.6), to which was then added 100 $\mu$L of avidin-ALP (*5000; DAKO D-365). The resultant mixture was allowed to stand at room temperature for 5 min and washed four times with an ALP buffer because a biotin-avidin system was used. After addition of AMPPD (100 $\mu$L, Lumigen PPD; Wako Pure Chemical Industries, Ltd., Japan), the mixture was transferred to a white plate. Ten minutes later, the amount of luminescence was measured. The results are shown in FIG. 1.

As a result, the protein amount of the hemolyzed solution has been presumed to be about 10 $\mu$g. Therefore, it has been presumed that, when the particles were at the concentration of 2.5% and at the surface area of 9.6E-0.3 m$^2$, the amount of proteins was too small and accordingly aggregation would take place during the reaction whereby it would be impossible to assay for those analytes that entered into the carriers. When particles with a size of 1 $\mu$m were used, the value, about 9.6E-03 m$^2$, seemed to be appropriate.

Example 2

Relation Between Antibody Amount and Signal

To 100 $\mu$L of 0.025% aqueous magnetic latex particle dilution (the same latex product as in Example 1 was used for the insoluble magnetic carrier particles) was added 5 $\mu$L of hemolyzed solution (prepared in the same manner as in Example 1), and the mixture was allowed to stand at room temperature for 5 min, to which was added an aliquot of biotinylated anti-HbA1c mAb (prepared in the same manner as in Example 1, at 0.048 mg/ml (50 $\mu$L, 2.4 $\mu$g), 0.0048 mg/ml (50 $\mu$L, 0.24 $\mu$g) or 0.00048 mg/ml (50 $\mu$L, 0.024 $\mu$g)). The mixture was allowed to stand at room temperature for 5 min and washed once with an ALP buffer (1% BSA, 50 mM imidazole, 150 mM NaCl, 1 mM MgCl$_2$, 0.1 mM ZnCl$_2$, 0.05% Tween 20; pH 7.6). Thereafter, 100 $\mu$L of avidin-ALP (the same reagent as in Example 1) was added thereto. The resultant mixture was allowed to stand at room temperature for 5 min and washed with an ALP buffer four times since a biotin-avidin system was used. Then 100 $\mu$L of AMPPD (the same reagent as that in Example 1) was added, and the mixture was transferred to a white plate. Ten minutes later, the amount of luminescence was measured.

Figure 2:
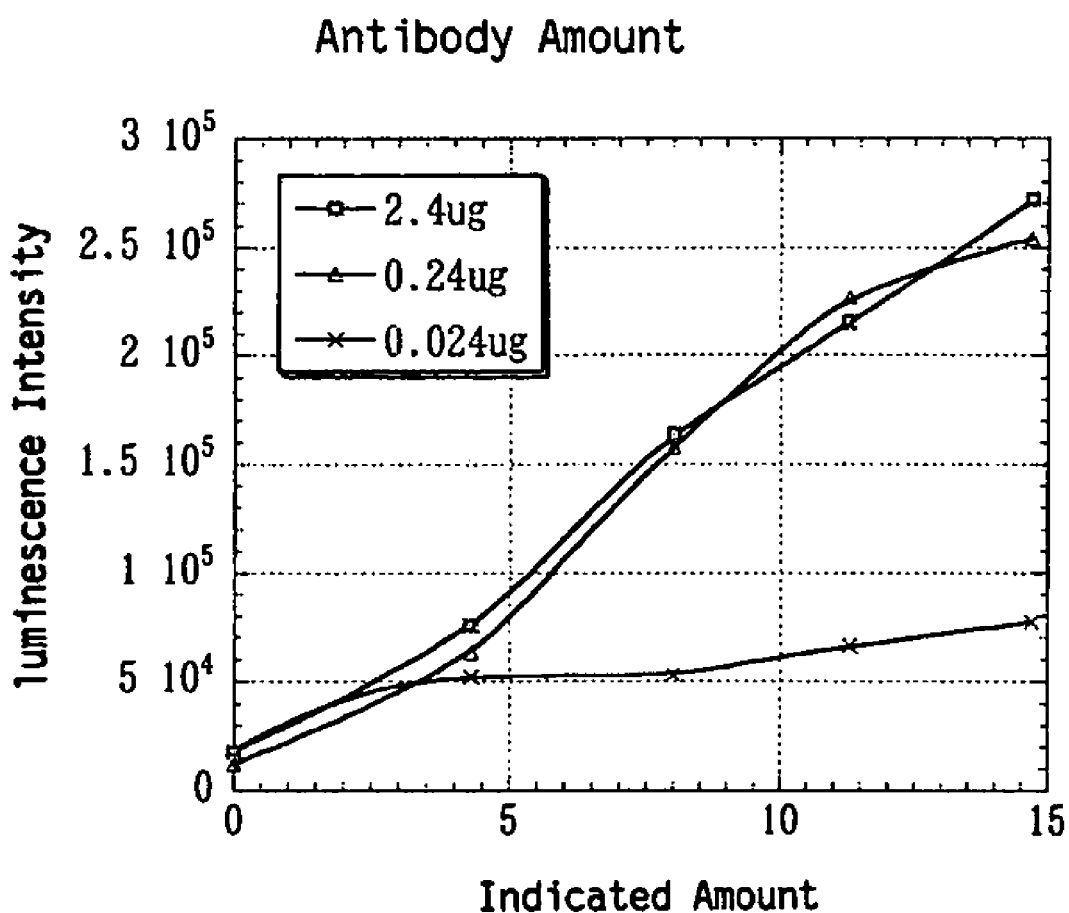
FIG. 2 shows the signal-antibody amount relationship between the resultant signals and antibodies existing in a system for HbA1c assay with labeled anti-HbA1c mAb, including the step of adsorbing HbA1c on magnetic latex particles.

The results are shown in FIG. 2. As a result, it has been found that about 0.25 µg was sufficient as the amount of anti-HbA1c mAb.

Example 3

Assays with Directly Labeled Antibodies

For the purpose of simplifying assays and improving reproducibility, anti-HbA1c mAb was directly labeled with ALP.

(1) Alkaline phosphatase (ALP; Oriental Yeast, Co., Ltd., Japan) was labeled with fluorescein isothiocyanate (FITC; DOJINDO, Japan). Firstly, ALP (10 mg/mL, 100 µL) was added to 0.1 M NaHCO$_3$ buffer (400 µL), to which was then added 10 µL of FITC solution (4 mg of FITC in dimethylformamide (DMF, 1 mL)) (AlP: FITC=1:10). The mixture was stirred at room temperature for 10 min and the resultant product was recovered using PD-10 (Pharmacia). For the elution, 0.1 M NaH$_2$PO$_4$ buffer, pH 7.5 was used. FITC-labeled ALP (1.7 mL) was recovered.

The above-prepared FITC-labeled ALP (ALP-FITC) was maleimidated. Firstly, the above-recovered ALP-FITC was concentrated with Centricon 30 (Millipore) to 500 µL. Thereafter, 10 µL of EMCS solution (N-(ε-maleimidocaproyloxy)-succinimide (EMCS, 6 mg) in DMF (1 mL)) was added (ALP-FITC: EMCS=1:20). The mixture was stirred at room temperature for 30 min and the resultant product was recovered using PD-10 (Pharmacia). For the elution, 0.1 M NaH$_2$PO$_4$ buffer, pH 6.3 containing 5 mM of ethylenediaminetetraacetic acid (EDTA) was used. A solution of maleimidated ALP-FITC (1.7 mL) was recovered.

In the meanwhile, the anti-HbA1c mAb (the same antibody as used in Example 1) was converted into an SH-form. Thus, 19.1 mg of anti-HbA1c mAb (52.4 µL) was added to 0.1 M NaH$_2$PO$_4$ buffer, pH 7.5 (450 µL), to which was then added 10 µL of AMSA solution (S-acetylmercaptosuccinic acid anhydride (AMSA, 6 mg) in DMF (1 mL)) (antibody: AMSA=1:50). The mixture was stirred at room temperature for 30 min, to which was then added 1 M Tris buffer, pH 7.0 (20 µL) containing 50 mM EDTA, and 1 M hydroxylamine hydrochloride solution, pH 7.0 (20 µL). The mixture was stirred at room temperature for 15 min and the resultant product was recovered using PD-10 (Pharmacia). For elution, 0.1 M NaH$_2$PO$_4$, pH 6.3 containing 5 mM EDTA was used. An SH-form antibody (IgG SH, 1.7 mL) was recovered.

Thereafter, a total amount of the above-prepared maleimidated ALP-FITC was mixed with a total amount of the above-prepared IgG SH. The mixing ratio was presumed to be ALP:IgG=1.5:1 (molar ratio). After the reaction at room temperature for 2 hr, the mixture was concentrated with Centricon (Millipore) to 500 µL and subjected to gel filtration (carrier used: Superose™ 12; Pharmacia) to give ALP-labeled anti-HbA1c mAb.

Figure 3:
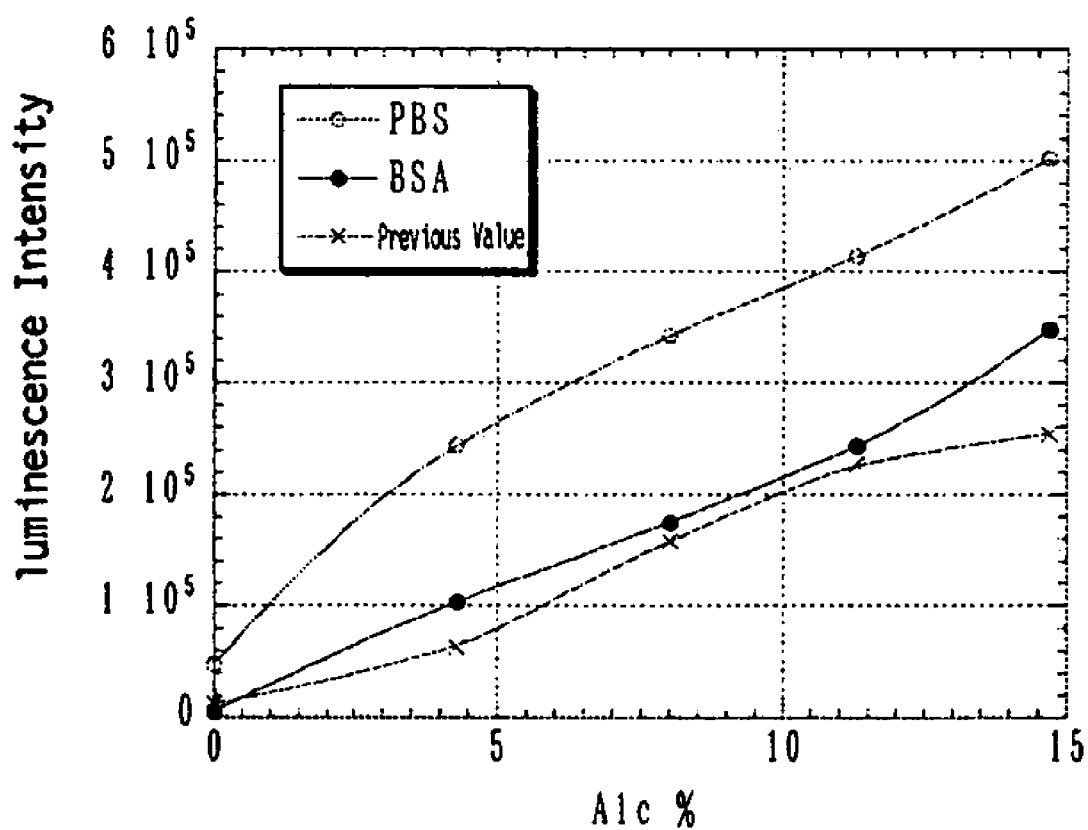
FIG. 3 shows the results when the label used is a directly detectable one in the HbA1c assay with labeled anti-HbA1c mAb, including the step of adsorbing HbA1c on magnetic latex particles.

(2) To 100 µL of 0.025% magnetic latex particle dilution (the same latex dilution as in Example 1) was added 5 µL of hemolyzed blood solution (the same blood sample as in Example 1.). The mixture was allowed to stand at room temperature for 5 min, to which was then added ALP-labeled anti-HbA1c mAb. For the antibody, 50 µL of 5 µg/ml IgG was added. An antibody dilution wherein the antibody was diluted with PBS-Tween and another antibody dilution wherein the antibody was diluted with BSA-containing buffer were also used for comparisons. The mixture was allowed to stand at room temperature for 5 min and then washed with PBS-Tween four times. After addition of AMPPD (100 µL, the same reagent as in Example 1), the mixture was transferred to a white plate. Fifteen minutes later, the amount of luminescence was measured. The results are shown in FIG. 3.

Figure 4:
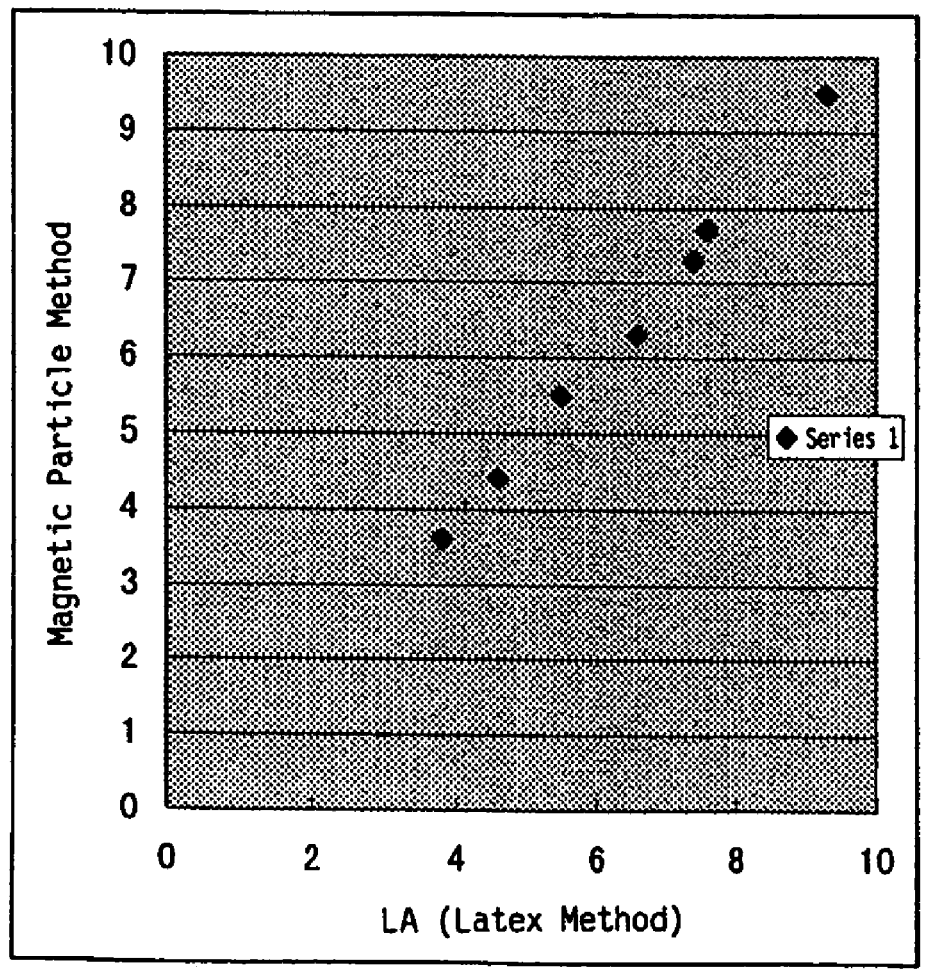
FIG. 4 shows the correlation between a latex aggregation method and an HbA1c assaying method with labeled anti-HbA1c mAb, including the step of adsorbing HbA1c on magnetic latex particles.

When protein coexists upon the addition of the antibody, it was observed that background lowered. As a result of lowering the background, an improvement in reproducibility can be expected. It has been verified that signal is increased as compared with the case of avidin-ALP. FIG. 4 shows the results of checking the correlation between the hemoglobin A1c (HbA1c) test reagent, "RAPIDIA AUTO HbA1c" (seller: FUJIREBIO Inc., Japan; manufacturer: SRL, Inc., Japan) with a latex aggregation method and the inventive method. Existence of a good correlation has been verified.

Example 4

Comparison Due to Variations in Insoluble Magnetic Carrier Particles

The same operations and reagents as in Example 3 were applied. The Fujikura Kasei latex particles (Fujikura Kasei Co., Ltd., Japan) as used in Examples 1 to 3 were compared with the VERITAS latex particles (VERITAS Corporation, Japan). Measurements were conducted where each total surface area of the magnetic particle reagents to be used for assays was set to be equal.

The VERITAS latex particles had a particle size of 2.8 µm, a particle concentration of 4.0E+09 particles/ml, an area (calculated) of 2.46E-11 and a surface area per assay of 9.59E-05m$^2$/particle (1 µL required for adjustment to m$^2$). The VERITAS latex particles were diluted with water to form a 100-fold dilution. The VERITAS latex particle dilution was used at 100 µL.

To 100 µL of each magnetic particle suspension (surface area: 9.59E-11 m$^2$) was added 5 µL of hemolyzed blood solution and the mixture was allowed to stand at room temperature for 5 min. Thereafter, ALP-labeled anti-HbA1c mAb was added to the mixture. For the antibody, 50 µL of 5 µg/ml IgG was added. The mixture was allowed to stand at room temperature for 5 min and washed with PBS-Tween four times, to which was added 100 µL of AMPPD (the same reagent as in Example 1). The resultant mixture was transferred to a white plate. Fifteen minutes later, the amount of luminescence was measured.

Figure 5:
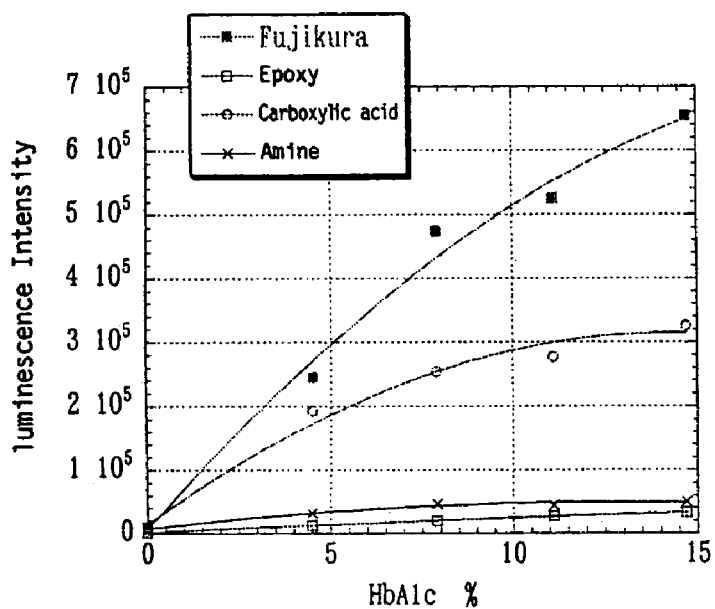
FIG. 5 shows the assay influence of variations among used insoluble magnetic carrier particles on the HbA1c assay with labeled anti-HbA1c mAb, including the step of adsorbing HbA1c on magnetic latex particles.
Figure 5:
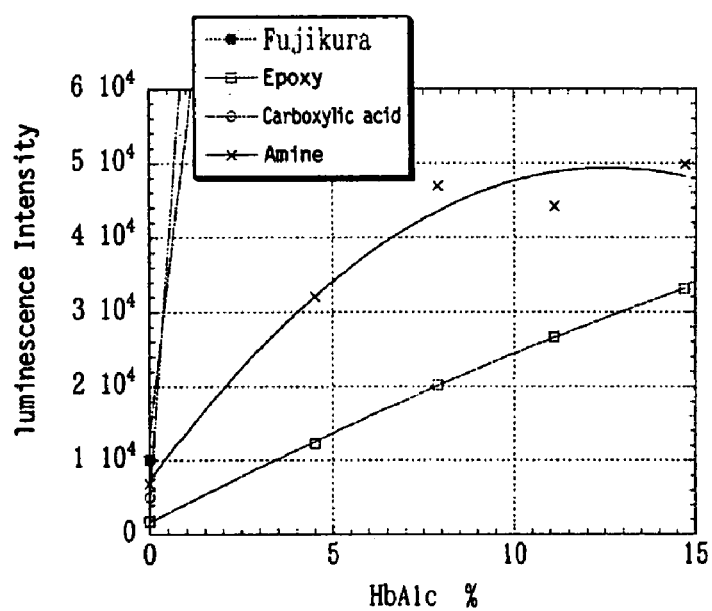

The results are shown in FIG. 5. For a calibrator, the hemoglobin A1c (HbA1c) test reagent, "RAPIDIA AUTO HbA1c" (seller: FUJIREBIO Inc., Japan; manufacturer: SRL, Inc., Japan) was used.

INDUSTRIAL APPLICABILITY

The immunoassay of the present invention allows simple, convenient and rapid measurements for antigenic substances in test samples without any troublesome pretreatment, thereby greatly facilitating the parallel treatment of a quite great number of samples simultaneously. In addition, such assay methods are suitably applicable to fully-automated instruments for clinical tests. Therefore, it will be possible to automate measuring steps and to carry out mass treatments. Further, in accordance with the present invention, there are advantages not only in terms of the assay per se but also manufacture of reagents. Thus, in general, in the manufacture of magnetic latex reagents (latex to which antigen, antibody, etc. are bound), it is not always easy to prepare reagents having the equal quality. Moreover, the know-how to prevent aggregation and precipitation during storage is needed. In general, the cost of latex materials merely occupies a minor part in diagnostic latex reagent expenses, but most of the reagent costs are attributable to the cost of biomaterials and the expenses required for-steps of coating said biomaterials on the latex particles. With this respect, according to the present invention, the insoluble magnetic carrier (such as latex) is neither substantially sensitized with any antigen nor with any antibody, thereby enabling the application of commercially available insoluble magnetic carriers (latex, etc.) for test reagents per se without any modification with the result that it will be not essential to newly manufacture a "latex reagent". In addition, the antibodies according to the present invention will be not always required to be purified products and their necessary amount will be greatly reduced as well. Thus, the production of test reagents becomes easier and quite great advantages are present in view of preservation stability.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

What is claimed is:

1. A quantitative immunoassay using an insoluble carrier particle which comprises
   (i) providing an insoluble magnetic carrier particle in a state substantially free of any adsorbed antigen and/or antibody,
   (ii) adsorbing an antigenic substance in a test sample on said insoluble magnetic carrier particle or binding said antigenic substance to said insoluble magnetic carrier particle,
   (iii) reacting said insoluble magnetic carrier particle with a labeled antibody specifically reactive with a solid-phase form of said antigenic substance, but substantially non-reactive with a native-state form of said antigenic substance, wherein said solid-phase form antigenic substance is attached to said insoluble magnetic carrier particle, and said native-state antigenic substance is in a liquid phase,
   (iv) washing said insoluble magnetic carrier particle, and
   (v) measuring the label on said labeled antibody captured by said solid-phase antigenic substance,
   wherein said antigenic substance in the test sample is hemoglobin antigen HbA1c.

2. The immunoassay according to claim 1, wherein said immunoassay comprises
   (A) adsorbing said antigenic substance in said test sample on said insoluble magnetic carrier particle or binding the said antigenic substance to said insoluble magnetic carrier particle, and
   (B) then reacting said antigenic substance with said labeled antibody, without removing said test sample from said insoluble magnetic carrier particle with washing.

3. The immunoassay according to claim 1, wherein said immunoassay comprises
   (a) reacting said labeled antibody with said insoluble magnetic carrier particle to which said antigenic substance in said test sample is adsorbed on or bound to,
   (b) then separating an unreacted labeled antibody from said insoluble magnetic carrier particle in the presence of a magnetic field action, and
   (c) measuring the label on the labeled antibody captured by said solid-phase antigenic substance.

4. The immunoassay according to claim 1, wherein said antibody is monoclonal.

5. The immunoassay according to claim 1, wherein said antibody is polyclonal.

6. The immunoassay according to claim 1, wherein said insoluble magnetic carrier particle is a particle which is substantially insoluble in an aqueous liquid medium and comprised of an organic polymer material phase and a magnetic material phase.

7. The immunoassay according to claim 1, wherein said insoluble magnetic carrier particle is a particle which comprises not only a coat phase made up of one or more organic polymer materials but also a core phase made up of one or more magnetic materials.

8. The immunoassay according to claim 1, wherein said insoluble magnetic carrier particle is a latex particle which has (a) an average particle size ranging from 0.01 to 20 microns and (b) a core made up of one or more magnetic materials.

9. The immunoassay according to claim 1, wherein said insoluble magnetic carrier particle is a latex particle which has an average particle size ranging from 0.1 to 6 microns and a core comprised of one or more magnetic materials.

10. The immunoassay according to claim 1, wherein said immunoassay is automated from dispensing said test sample to attaining test results with a clinical chemistry autoanalyzer suited for magnetic particles.

* * * * *